United States Patent
Penney et al.

(10) Patent No.: US 8,071,580 B2
(45) Date of Patent: Dec. 6, 2011

(54) MEDIUM-CHAIN LENGTH FATTY ALCOHOLS AS STIMULATORS OF HEMATOPOIESIS

(75) Inventors: Christopher Penney, Pierrefonds (CA); Lyne Gagnon, Laval (CA); Jean Barabé, Montreal (CA)

(73) Assignee: Prometic Biosciences Inc., Laval, Quebec (CA)

( * ) Notice: Subject to any disclaimer, the term of this patent is extended or adjusted under 35 U.S.C. 154(b) by 0 days.

(21) Appl. No.: 11/663,888

(22) PCT Filed: Sep. 29, 2005

(86) PCT No.: PCT/CA2005/001490
§ 371 (c)(1),
(2), (4) Date: Mar. 27, 2007

(87) PCT Pub. No.: WO2006/086871
PCT Pub. Date: Aug. 24, 2006

(65) Prior Publication Data
US 2008/0051324 A1    Feb. 28, 2008

Related U.S. Application Data

(60) Provisional application No. 60/614,478, filed on Oct. 1, 2004.

(51) Int. Cl.
*A61K 31/33* (2006.01)
*A61K 31/045* (2006.01)

(52) U.S. Cl. ....................... 514/183; 514/724
(58) Field of Classification Search ............... 514/183, 514/724
See application file for complete search history.

(56) References Cited

U.S. PATENT DOCUMENTS

| | | | |
|---|---|---|---|
| 4,812,443 A | 3/1989 | Takak et al. | |
| 4,897,426 A * | 1/1990 | Llinas et al. | 514/724 |
| 4,962,129 A | 10/1990 | Revici | |
| 2002/0028515 A1 * | 3/2002 | Talmadge et al. | 435/458 |
| 2002/0076443 A1 * | 6/2002 | Stein et al. | 424/486 |
| 2003/0072720 A1 * | 4/2003 | Nevo | 424/49 |
| 2004/0147599 A1 | 7/2004 | Gagnon et al. | |
| 2005/0020487 A1 | 1/2005 | Klaus et al. | |
| 2006/0128800 A1 | 6/2006 | Penney et al. | |

FOREIGN PATENT DOCUMENTS

| | | |
|---|---|---|
| EP | 0 166 436 A2 | 1/1986 |
| WO | 95/30413 A1 | 11/1995 |
| WO | 02/083120 A2 | 10/2002 |
| WO | 2004/069237 A1 | 8/2004 |

OTHER PUBLICATIONS

Macdougall, I. 'Novel Erythropoiesis-Stimulating Agents: A New Era in Anemia Management' Clincal Journal of the American Society of Nephrology, vol. 3, p. 200-207, 2008.*

Hisha et al. "Isolation and Identification of Hematopoietic Stem Cell-Stimulating Substances from Kampo (Japanese Herbal) Medicine, Juzen-Taiho-To" Blood, 1997, vol. 90, No. 3, pp. 1022-1030.

Bug et al. "Valproic Acid Stimulates Proliferation and Self-Renewal of Hematopoietic Stem Cells" Cancer Research, 2005, vol. 65, No. 7, pp. 2537-2541.

Balleari et al., "In Vivo Effects of Thymustimulin on Hematopoiesis of Mice Treated with Cyclophosphamide," Clin. Immunol. Immunopathol. 68:363-367, 1993 (abstract only).

Duffy et al., "Identification of a Pharmacophore for Thrombopoietic Activity of Small, Non-Peptidyl Molecules. 1. Discovery and Optimization of Salicylaldehyde Thiosemicarbazone Thrombopoietin Mimics," J. Med. Chem. 45:3573-3575, 2002 (published on web Jul. 19, 2002).

Duffy et al., "Hydrazinonaphthalene and Azonaphthalene Thrombopoeitin Mimics are Nonpeptidyl Promoters of Megakaryocytopoiesis," J. Med. Chem. 44:3730-3745, 2001 (published on web Sep. 13, 2001).

Ito et al., "Maitake Beta-Glucan Enhances Granulopoiesis and Mobilization of Granulocytes by Increasing G-CSF Production and Modulating CXCR4/SDF-1 Expression," Int. Immunopharmacol. 9:1189-1196, 2009 (abstract only).

Kusano et al., "A Potential Therapeutic Role for Small Nonpeptidyl Compounds that Mimic Human Granulocyte Colony-Stimulating Factor," Blood 103:836-842, 2004 (pre-published online Sep. 25, 2003).

Rodgers et al., "Effect of Angiotensin II and Angiotensin(1-7) on Hematopoietic Recovery after Intravenous Chemotherapy," Cancer Chemother. Pharmacol. 51:97-106, 2003 (abstract only; Epub Dec. 19, 2002).

Wang et al., "Role of the Spleen in Cyclophosphamide-Induced Hematosuppression and Extramedullary Hematopoiesis in Mice," Arch. Med. Res. 40:249-255, 2009 (abstract only; Epub Jun. 2, 2009).

International Search Report from International Application No. PCT/CA2005/001490, dated Nov. 1, 2005 (date of completion of search) and Dec. 7, 2005 (date of mailing of report).

* cited by examiner

*Primary Examiner* — Brandon Fetterolf
*Assistant Examiner* — Christopher R Stone
(74) *Attorney, Agent, or Firm* — Clark & Elbing LLP

(57) ABSTRACT

Medium-chain length fatty alcohols such as octanol, decanol, dodecanol, or analogues thereof can be used as a stimulator of hematopoiesis, hematopoietic stem cell proliferation, and/or proliferation of one or more of the progenitors of red or white blood cells (e.g., erythrocyte, leukocyte, neutrophil, granulocyte, megakaryocyte, or any combination thereof). It also relates to the treatment of myelosuppression; in particular, this includes the treatment of anemia and/or neutropenia associated with chemotherapy and/or radiotherapy. Moreover, anemia arising from chronic renal failure or treatment of HIV-infected patients with AZT (zidovudine), or other inhibitors of reverse transcriptase, can be treated. Furthermore, neutropenia arising from infections, hematologic diseases, or nutritional deficiencies can be treated. It also relates to reducing drug toxicity and enhancing drug efficiency.

30 Claims, 2 Drawing Sheets

MEDIUM-CHAIN LENGTH FATTY ALCOHOLS AS STIMULATORS OF HEMATOPOIESIS

CROSS REFERENCE TO RELATED APPLICATIONS

This application is a U.S. national stage of International Patent Application No. PCT/CA2005/001490, filed 29 Sep. 2005, which designated the U.S. and claims the benefit of provisional U.S. Appln. No. 60/614,478 filed Oct. 1, 2004; the contents of each of which are incorporated by reference herein.

FIELD OF THE INVENTION

The present invention relates to the treatment of myelosuppression. In particular, this includes the treatment of anemia and/or neutropenia associated with the use of chemotherapy and/or radiotherapy. The present invention may also find use for the treatment of anemia arising from chronic renal failure or treatment of HIV-infected patients with AZT (zidovudine) and/or for the treatment of neutropenia arising from infections, hematologic diseases, or nutritional deficiencies. The present invention also relates to reducing drug toxicity and enhancing drug efficiency. In particular, the present invention relates to the use of medium-chain length fatty alcohols such as octanol, decanol, dodecanol, or analogues thereof as a stimulator of hematopoiesis, hematopoietic stem cell proliferation, and/or proliferation of one or more of the progenitors of red or white blood cells (e.g., erythrocyte, leukocyte, neutrophil, granulocyte, megakaryocyte, or any combination thereof).

BACKGROUND OF THE INVENTION

Chemotherapy refers to the use of cytotoxic agents such as, but not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, and chlorambucil to eradicate cancer cells and tumors. However, these agents are non-specific and, particularly at high doses, they are toxic to normal, rapidly dividing cells. Ionizing radiation is also toxic to normal, rapidly dividing cells. This often leads to various side effects in patients undergoing chemotherapy and radiotherapy. Myelosuppression, a severe reduction of blood cell production in bone marrow, is one such side effect. It is characterized by anemia, leukopenia, neutropenia, agranulocytosis, and thrombocytopenia. Severe chronic neutropenia is also characterized by a selective decrease in the number of circulating neutrophils and an enhanced susceptibility to bacterial infections.

The essence of treating cancer with chemotherapeutic drugs is to combine a mechanism of cytotoxicity with a mechanism of selectivity for highly proliferating tumor cells over host cells. However, it is rare for chemotherapeutic drugs to have such selectivity. The cytotoxicity of chemotherapeutic agents limits administrable doses, affects treatment cycles, and seriously jeopardizes the quality of life for the cancer patient. Similar drawbacks affect the treatment of cancer with radiotherapy.

Although other normal tissues may also be adversely affected, bone marrow is particularly sensitive to proliferation-specific treatments such as chemotherapy or radiotherapy. Acute and chronic bone marrow toxicity, which is a common side effect of cancer therapies, leads to decreases in blood cell counts and anemia, leukopenia, neutropenia, agranulocytosis, and/or thrombocytopenia. One cause of such effects is a decrease in the number of replicating hematopoietic cells (e.g., pluripotent stem cells and other progenitor cells) caused by both a lethal effect of cytotoxic agents or radiation on these cells and by differentiation of stem cells provoked by a feedback mechanism induced by the depletion of more mature marrow compartments. The second cause is a reduction in self-renewal capacity of stem cells, which is also related to both direct (mutation) and indirect (aging of stem cell population) effects (Tubiana, M., et al., *Radiotherapy and Oncology* 29:1-17, 1993). Thus, cancer treatments often result in a decrease in red blood cells or erythrocytes and white blood cells or leukocytes (which consist predominantly of neutrophils) in the general circulation.

Erythrocytes are non-nucleated biconcave disk-like cells which contain hemoglobin and are essential for the transport of oxygen. Hemoglobin is a tetrapeptide which contains four binding sites for oxygen. Anemia refers to that condition which exists when there is a reduction below normal in the number of erythrocytes, the quantity of hemoglobin, or the volume of packed red blood cells in the blood as characterized by a determination of the hematocrit. The hematocrit or "red blood cell volume" is considered to be a particularly reliable indicator of anemia. Typically, in normal adults, average values for red blood cell count ($10^6$/mm$^3$), hemoglobin (g/100 mL), and hematocrit (the volume of packed red blood cells in mL/100 mL) for females and males (at sea level) are 4.8±0.6 and 5.4±0.9, 14.0±2.0 and 16.0±2.0, and 42.0±5.0 and 47.0±5.0, respectively, as described in *Harrison's Principles of Internal Medicine*, 8$^{th}$ Edition, Appendix-Table A-5, McGraw Hill (1977). In normal humans, erythrocytes are produced by the bone marrow and released in the circulation, where they survive approximately 120 days. They are subsequently removed by the monocyte-phagocyte system.

Anemia is a symptom of various diseases and disorders. Therefore, anemia may be classified in terms of its etiology. For example, aplastic anemia is characterized by absence of regeneration of erythrocytes and is resistant to therapy. In such patients, there is a marked decrease in the population of myeloid, erythroid, and thrombopoietic stem cells, which results in pancytopenia. Hemolytic anemia arises from shortened survival of erythrocytes and the inability of the bone marrow to compensate for their decreased life span. It may be hereditary or may result from chemotherapy, infection, or an autoimmune process. Iron deficiency anemia refers to a form of anemia characterized by low or absent iron stores, low serum iron concentration, low hemoglobin concentration, or low hematocrit, etc. Iron deficiency is the most common cause of anemia. Pernicious anemia, which most commonly affects adults, arises from a failure of the gastric mucosa to secrete adequate intrinsic factor, resulting in malabsorption of vitamin B12. Sickle cell anemia arises from a genetically determined defect in hemoglobin synthesis. It is characterized by the presence of sickle-shaped erythrocytes in the blood. The above are only exemplary of the many different anemias known to medicine. However, within the context of this invention, it is of particular interest to address anemia associated with the use of chemotherapy or radiotherapy in the treatment of cancer. According to a statement published in *BioWorld Today* (page 4; Jul. 23, 2002), approximately 1.2 million cancer patients will undergo cytotoxic chemotherapy in the United States this year and about 800,000 or 67% of them will become anemic. Additionally, anemia is also associated with end-stage renal disease as is the case for patients who require regular dialysis or kidney transplantation for survival. This falls under the umbrella of chronic renal failure or the clinical situation in which there is a progressive and usually irreversible decline in kidney function.

Erythropoietin (EPO) is a glycoprotein with a molecular weight of 34,000 which is produced in the kidney. EPO stimulates the division and differentiation of committed erythroid progenitors in the bone marrow (BFU-E cells) and maintains cell viability (inhibition of apoptosis of BFU-E and CFU-E cells). The biological effects of EPO are receptor mediated. Amino acid identity amongst different animals is 92% between human EPO and monkey EPO and 80% between human EPO and mouse EPO. The primary stimulus for the biosynthesis of EPO is tissue hypoxia. However, as may be seen from the above, EPO has significant therapeutic potential for the treatment of certain anemias. For example, EPO can be used to treat anemia arising from a diminished endogenous production of EPO, which may result from a damaged or nonfunctional kidney (e.g., chronic renal failure as discussed above). Alternatively, EPO can be used to treat anemia arising from damaged bone marrow and subsequently diminished proliferation of erythrocyte progenitors (e.g., BFU-E cells) which results from treatment of cancer patients with cytotoxic chemotherapy or radiotherapy (as also discussed above). Various forms of recombinant EPO are available on the market. They differ by their expression system used for their manufacture and by their sites and degree of glycosylation of the protein. Epoetin alpha is expressed in CHO cells and is available under the trade name of PROCRIT®, EPOGEN®, or EPREX®. Like EPO, Epoetin alpha has three N-linked glycosylation sites at asparagine (Asn) residues; Asn 19, Asn 33, and Asn 78. Epoetin beta is also N-glycosylated at three sites. Epoetin omega is N-glycosylated at Asn 24, Asn 28, and Asn 83 and partially O-glycosylated at serine (Ser 126). Recently, a hyperglycosylated version of EPO has been approved which contains five N-linked glycosylation sites. It is a slow or extended release form of epoetin alpha available under the trade name of ARANESP®. This protein displays enhanced biological activity compared to the natural form, due to its approximately three-fold longer serum half-life. However, the use of these glycosylated proteins is expensive and restricted since they have to be produced by recombinant technology.

In individuals with normal blood cell counts, neutrophils constitute approximately 60% of the total leukocytes (*SI Units Conversion Guide*, 66-67, 1992, N. Engl. J. Med. Books). However, as many as one in three patients receiving chemotherapy treatment for cancer may suffer from neutropenia. Mean normal neutrophil counts for healthy human adults are on the order of 4400 cells/µL, with a range of 1800-7700 cells/µL. A count of 1,000 cells/µL to 500 cells/µL is moderate neutropenia and a count of 500 cells/µL or less is severe neutropenia. Patients in myelosuppressive states are prone to infection and frequently suffer from blood-clotting disorders, requiring hospitalization. Lack of neutrophils and platelets is the leading cause of morbidity and mortality following cancer treatments and contributes to the high cost of cancer therapy. In these above-mentioned conditions, the use of any agent capable of inhibiting neutrophil apoptosis or stimulating neutrophil activation and mobilization can be of therapeutic value. Efforts to restore the patient's immune system after chemotherapy involve the use of hematopoietic growth factors to stimulate remaining stem cells to proliferate and differentiate into mature infection fighting cells.

In bone marrow transplantation, a phenomenon known as "mobilization" has also been exploited to harvest greater numbers of stem/progenitor cells from peripheral blood. This method is currently used for autologous or allogeneic bone marrow transplantation. Growth factors are used to increase the number of peripheral progenitor stem cells to be harvested before myeloablative therapy and infusion of progenitor stem cells.

Post-therapy bone marrow transplantation can also counter neutropenia. However, these treatments require 10-15 days of treatment which leaves patients vulnerable to infection. Agents capable of stimulating bone marrow stem cells can facilitate and accelerate stem cells engraftment thus shortening the neutropenic window following bone marrow transplantation.

Although hematopoietic growth factors such as granulocyte-macrophage colony stimulating factor (GM-CSF) and granulocyte colony stimulating factor (G-CSF) can exert such actions, their use is expensive since they have to be produced by recombinant technology. Such post-therapeutic ameliorative treatments are unnecessary if patients are "chemoprotected" from immune suppression.

Therefore, there is a need for novel compositions and methods to reduce the undesirable side effects of myelosuppressive states induced by chemotherapy and/or radiotherapy.

SUMMARY OF THE INVENTION

The present invention satisfies the need for chemoprotective agents by providing a novel method for the stimulation of the hematopoietic system in a patient. The present invention also provides a novel method for treating the myelosuppressive effects of chemotherapy, radiotherapy, or any other situation in which the stimulation of the hematopoietic system can be of therapeutic value such as, but not limited to, anemia, leukopenia, neutropenia, agranulocytosis, thrombocytopenia, and/or bone marrow transplantation.

In accordance with this method, a composition comprising one or more medium-chain fatty alcohols (e.g., octanol, decanol, dodecanol) or alkyl esters thereof in a pharmaceutically acceptable carrier is administered to a patient in an amount effective to stimulate hematopoiesis. This may significantly reduce the adverse effects of chemotherapy and radiotherapy (e.g., myelosuppression).

It is an objective of the present invention relates to the use of medium-chain fatty alcohols (e.g., octanol, decanol, dodecanol) or alkyl esters thereof as hematopoiesis stimulating factors or chemoprotective agents.

Another object of the present invention relates to the use of medium-chain fatty alcohols (e.g., octanol, decanol, dodecanol) or alkyl esters thereof for the treatment of myelosuppression arising from chemotherapy and/or radiotherapy.

It is an object of the present invention to provide a method effective for providing chemoprotection of a patient.

Another object of the present invention is to provide a method effective for increasing the efficacy of chemotherapy and radiotherapy in a patient.

Still another object of the present invention is to provide a method effective for reducing or eliminating chemotherapy- or radiotherapy-induced anemia or neutropenia in a patient.

Another object of the present invention is to provide a method for treating neutropenia arising from a hematologic disease, or infection, or a nutritional deficiency, or drug-induced neutropenia.

Yet another object of the present invention is to provide a method for treating anemia arising from chronic renal failure, or end-stage renal disease, or arising from a medical or surgical procedure, or drug-induced anemia.

Finally, another object of the present invention is to provide a method that causes minimal or no adverse effects to the patient.

These and other objects, features and advantages of the present invention will become apparent after a review of the following detailed description and the appended claims.

BRIEF DESCRIPTION OF THE DRAWINGS

FIG. 3 shows the effect of octanol, decanol, or dodecanol on spleen red cell count.

DETAILED DESCRIPTION OF THE INVENTION

Figure 1:
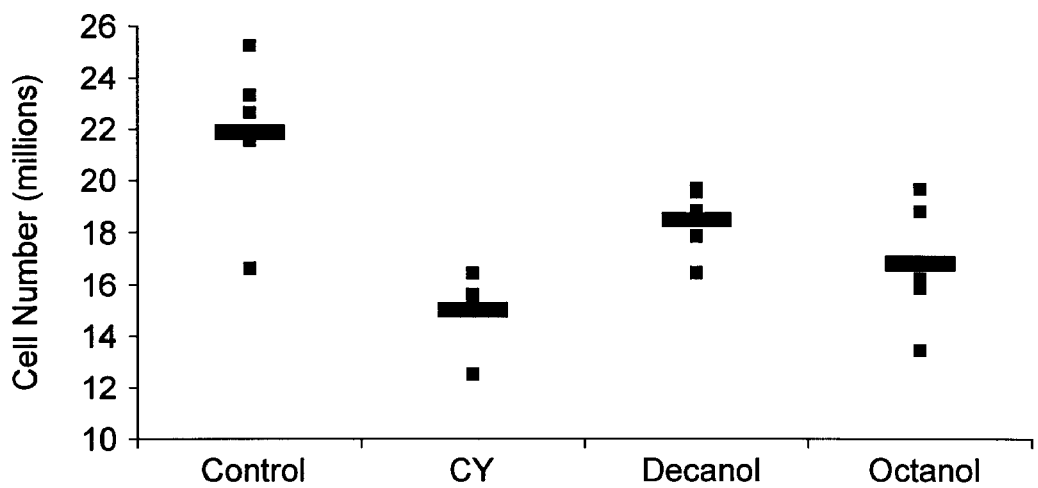
FIG. 1 shows the effect of octanol or decanol on bone marrow white cell count.

Chemotherapy and radiotherapy destroy hematopoietic cells in bone marrow. Subsequently, the patient can be severely depleted in erythrocytes, platelets, and neutrophils. Anemia results in fatigue, a lack of energy and shortness of breath. Thrombocytopenia leads to prolonged clotting time and bleeding disorders. Neutropenia places the patient at increased risk of infection. Myelosuppression is a dose-limiting factor in cancer treatment.

The present invention relates to a method of restoring the patient's hematopoietic system. Current methods employed to do the same make use of cytokines or glycoprotein growth factors. For example, erythropoietin can be used to stimulate the proliferation and maturation of responsive bone marrow erythroid cells. Erythropoietin is approved for human use for the treatment of anemia where appropriate: e.g., anemia arising from the inability to produce a sufficient number of erythrocytes. However, there are limitations which restrict the use of erythropoietin. Indeed, many of these limitations are common to the medical use of recombinant glycoprotein cytokines—availability, toxicity, and efficacy, especially with chronic use. For example, some patients treated with recombinant human erythropoietin develop an immune response to the glycoprotein which results in pure red cell aplasia. When the latter occurs, the antibody developed to the recombinant protein also attacks the patient's equivalent or endogenous protein. Subsequently, the patient develops a worst anemia than before drug treatment.

Other hematopoietic growth factors can also be used to restore the patient's hematopoietic system which include granulocyte-colony stimulating factor (G-CSF), stem cell factor (SCF), and granulocyte macrophage-colony stimulating factor (GM-CSF). G-CSF and GM-CSF can shorten the total period of neutropenia and thrombocytopenia but there still remains a significant window during which the patient is susceptible to infection and is deficient in blood clotting capabilities.

Medium-chain fatty alcohols refer to aliphatic alkyl alcohols having carbon chain lengths of eight (C8, octanol or octadecyl alcohol), ten (C10, decanol or decyl alcohol), or twelve (C12, dodecanol or dodecyl alcohol). Unlike shorter chain alcohols, these alcohols are poorly soluble in water. Nonetheless, medium-chain fatty alcohols enjoy widespread industrial use and are found in an array of products which include plasticizers, solvents, herbicides, perfumes, and surface active agents. More importantly, medium-chain fatty alcohols are nontoxic materials. For example, according to part 172 of the Code of Federal Regulations, the U.S. Food and Drug Administration recognizes that octanol, decanol, and dodecanol are safe additives for use in food. The Registry of Toxic Effects of Chemical Substances (National Institute for Occupational Safety and Health) reports an $LD_{50}$ (oral, rats) of 3.2 g/kg body weight for octanol and 4.7 g/kg body weight for decanol, which is essentially nontoxic.

Until the unexpected findings described herein, the effectiveness of medium-chain fatty alcohols such as octanol, decanol, dodecanol, or alkyl esters thereof for the stimulation of hematopoiesis and the subsequent production of erythrocytes and neutrophils from erythroid and myeloid progenitor cells was unknown. A similar activity was described in our international applications PCT/CA02/00535 and PCT/GB04/00457 in which it was disclosed that medium-chain fatty acids and triglycerides are able to stimulate hematopoiesis and the subsequent production of erythrocytes and neutrophils. The present discovery is unexpected because, unlike the prior art, it is the ten and twelve carbon chain length alcohols which have consistently significant biological activity whereas in the prior art, it was the eight and ten carbon chain length carboxylic acids which have consistently significant biological activity. Therefore, significant biological activity is determined by more than the ability to tolerate a polar head group (e.g., hydroxyl, carboxylate) at the end of a hydrocarbon chain. In fact, another polar head group, an aldehyde moiety, resulted in compounds which were not able to stimulate hematopoiesis.

The present invention may stimulate hematopoiesis in a mammal, including a human using one or more medium-chain fatty alcohols of formula $H_3C(CH_2)_nOH$, wherein n is an integer from 7 to 11, and alkyl esters thereof. It can be used to treat the myelosuppressive effects of chemotherapy, radiotherapy, or any other situation in which the stimulation of the hematopoietic system can be of therapeutic value such as, but not limited to, anemia, leukopenia, neutropenia, agranulocytosis, thrombocytopenia, and/or bone marrow transplantation.

A pharmacologically effective amount of the medium-chain fatty alcohols and alkyl esters thereof is used. Such an effective amount may be determined by varying its dose to achieve the desired therapeutic affect(s) such as, for example, reducing the adverse effects of chemotherapy and/or radiotherapy. Medium-chain fatty alcohols and alkyl esters thereof as the active pharmaceutical ingredient(s) can be formulated in a pharmaceutical composition with a pharmaceutically acceptable carrier.

Examples of pathological conditions which may be treated include, but are not limited to: myelosuppression arising from chemotherapy and/or radiotherapy, and subsequent anemia and immunosuppression; chronic or transient neutropenia arising from hematologic diseases such as chronic idiopathic neutropenias, or from bacterial or viral infections, or a nutritional deficiency, or drug-induced neutropenia; anemia arising from chronic renal failure, especially in those patients with end-stage renal disease, or from medical procedures such as orthopedic surgery or the use of anti-retroviral drugs. Chemotherapy- and/or radiotherapy-induced anemia or neutropenia may be reduced or eliminated.

Chemoprotection of a mammal, including a human, may also be provided. The efficacy of chemotherapy and radiotherapy in a mammal, including a human, may be increased thereby and side effects avoided. Chemotherapy and/or radiotherapy, in combination with chemoprotection, may achieve a better therapeutic benefit for its recipient.

Treatment preferably causes minimal or no adverse effects to its recipient.

In a preferred embodiment of the present invention, it is decanol (the ten carbon chain length alcohol) and/or dodecanol (the twelve carbon chain length alcohol) which are employed as the active pharmaceutical ingredient or medicament. Additionally, where appropriate for preparation of a drug with desired physical chemical properties or in a prodrug format (e.g., susceptible to nonspecific esterases), short chain alkyl esters (one to four carbon atoms) may also be prepared for use as the medicament. However, this does not preclude the use of the less biologically active eight carbon chain length alcohol either as octanol or a short chain alkyl ester wherein the acid component is acetic, propionic, or butyric acid. Alternatively, it is even possible to make an alkyl ester which is derived from the condensation of a medium-chain fatty alcohol with a medium-chain fatty acid. Similarly, other obvious chemical modifications to anyone skilled in the art falls within the scope of this invention. Such obvious modifications include other prodrug formats including derivitization of the alcohol by attachment to sugars, amino acids, and peptides which may also serve to improve water solubility of the alcohol. In the opposite direction, a more active agent with decreased water solubility might be obtained by esterification of caprylic or capric acid with medium-chain fatty alcohols of this invention.

The present invention relates to the use of medium-chain fatty alcohols or alkyl esters thereof as a hematopoiesis activation or growth factor and, more particularly, as a stimulator of the production of erythrocyte and neutrophil progenitor cells. When used in chemotherapy and radiotherapy, medium-chain fatty alcohols are administered before, during and/or after the treatment in order to shorten the period of anemia and/or neutropenia and to accelerate the replenishment of the hematopoietic system. Furthermore, it is possible to use a combination of medium-chain fatty alcohols along with their alkyl esters thereof or other analogues at multiple points relative to treatment with chemotherapy and/or radiotherapy. Alternatively, it is possible to administer the combination simultaneously: before, during and/or after treatment with chemotherapy and/or radiotherapy. In severe anemia or neutropenia, the medium-chain fatty alcohol is used as the therapeutic agent. Medium-chain fatty alcohols can also be used after bone marrow transplantation in order to stimulate bone marrow stem cells thus shortening the time period for recovery from anemia and neutropenia.

As used herein, medium-chain fatty alcohols such as octanol, decanol or dodecanol refers to a composition comprising said active ingredient and one or more pharmaceutically acceptable carriers.

As used herein, the term "pharmaceutically acceptable carrier" refers to a substance that does not interfere with the physiological effects of medium-chain fatty alcohols such as octanol, decanol or dodecanol and that is not toxic to mammals, including humans.

The octanol, decanol or dodecanol of the present invention may be formulated using octanol, decanol or dodecanol and pharmaceutically acceptable carriers by methods known to those skilled in the art (*Merck Index*, Merck & Co., Rahway, N.J.). These compositions include, but are not limited to, solids, liquids, oils, emulsions, gels, aerosols, inhalants, sprays, capsules, pills, patches, and suppositories.

All methods may include the step of bringing the active ingredient(s) into association with the carrier which constitutes one or more accessory ingredients.

As used herein, the term "chemotherapy" refers to a process of killing proliferating cells using a cytotoxic agent. The phrase "after chemotherapy" is meant to cover all situations in which a composition is administered after the administration of a cytotoxic agent regardless of any prior administration of the same and also regardless of the persistence of the effect of the administered cytotoxic agent.

When the method of this invention is applied to chemotherapy, octanol, decanol, or dodecanol can be administered prior to, during, or subsequent to the chemotherapy (i.e., prior to, during, or subsequent to the administration of a cytotoxic agent).

By "cytotoxic agent" is meant an agent which kills highly proliferating cells: e.g., tumors cells, virally infected cells, or hematopoietic cells. Examples of a cytotoxic agent which can be used to practice the invention include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, chlorambucil, and an agonist of any of the above compounds. A cytotoxic agent can also be an antiviral agent: e.g., AZT/zidovudine (i.e., 3'-azido-3'-deoxythymidine) or 3TC/lamivudine (i.e., 3-thiacytidine).

As used herein, the term "chemoprotection" refers to protection provided to a mammal, including a human, from the toxic effects arising from treatment of the mammal with a chemotherapeutic agent. Most often, the latter is a cytotoxic agent whose therapeutic effect arises from its ability to interfere with or inhibit some aspect of DNA replication, RNA transcription, or subsequent translation of protein. Therefore, a chemoprotective agent refers to any compound administered to a mammal which would protect the mammal, or facilitate the recovery of the mammal, from the toxic effects resulting from treatment of the mammal with a chemotherapeutic agent.

Anemia can be diagnosed and its severity can be determined by a person skilled in the art. The term "anemia" may refer to that condition which exists when there is a reduction below normal in the number of erythrocytes, the quantity of hemoglobin, or the volume of packed red blood cells. Such clinical criteria are subject to variability. Without limitation, anemia may be the result of a reduction in the mass of circulating red blood cells. Efficacy of treatment can also be determined by a person skilled in the art. It may provide a palliative effect.

Neutropenia can be diagnosed and its severity can be determined by a person skilled in the art. The term "neutropenia" may refer to that condition which exists when there is a reduction below normal in the number of neutrophils. Such clinical criteria are subject to variability. Efficacy of treatment can also be determined by a person skilled in the art. It may provide a palliative effect.

In one preferred embodiment, the pharmaceutical composition is in a form suitable for oral, sublingual, rectal, topical inhalation (nasal spray), intramuscular, intradermal, subcutaneous, or intravenous administration.

It will be appreciated that the amount of a composition of the invention required for use in the treatment will vary with the route of administration, the nature of the condition being treated, the age and condition of the patient, and will ultimately be at the discretion of the attending physician. The desired dose may be conveniently presented in a single dose or as divided doses taken at appropriate intervals, for example as two, three or more doses per day as necessary to effect or bring about treatment. The term "treatment" or "treating" includes any therapy of existing disease or condition and prophylaxis of the disease or condition (e.g., anemia, neutropenia) in a mammal, including a human. This includes (a) preventing the disease or condition from occurring in a patient which may be predisposed to the disease but has not yet been diagnosed as having it, (b) inhibiting or arresting the development of the disease or condition and (c) relieving the disease or condition by causing its regression or the amelioration of one or more symptoms.

While it is possible that, for use in medical treatment, medium-chain fatty alcohols such as octanol, decanol, or dodecanol may be administered as the pure chemical, it is preferable to present the active pharmaceutical ingredient as a pharmaceutical formulation or composition. A nontoxic composition is formed by the incorporation of any of the normally employed excipients such as, for example but not limited to, mannitol, lactose, trehalose, starch, magnesium stearate, talcum, cellulose, carboxymethyl cellulose, glucose, gelatin, sucrose, glycerol, magnesium carbonate, sodium citrate, sodium acetate, sodium chloride, sodium phosphate, and glycine.

In a preferred embodiment of the invention, the amount of active ingredient administered is such that the concentration in the blood (free and/or bound to serum albumin) is greater than 1 µM. In other embodiments, the concentration in the blood may be greater than 1 mM. In another preferred embodiment of the invention, it might be necessary to achieve a sufficient local concentration of an active pharmaceutical ingredient to obtain a biologically or medically significant effect in a target tissue (e.g., bone marrow). Such a relatively high concentration of active pharmaceutical ingredient may be required, at least at the target tissue, as it may be necessary for the octanol, decanol, or dodecanol of the present invention to form a micelle or aggregate structure in order to elicit a biological response. A single dose may be comprised of a total amount from about 1 g to about 10 g of active ingredient (and any intermediate ranges thereof).

In another embodiment, the pharmaceutical composition is in a form suitable for enteral, mucosal (including sublingual, pulmonary, and rectal), parenteral (including intramuscular, intradermal, subcutaneous, and intravenous), or topical administration. The formulations may, where appropriate, be conveniently presented in discrete dosage units and may be prepared by any of the methods well known in the art of pharmacy. All methods include the step of bringing into association the active pharmaceutical ingredient with liquid carriers or finely divided solid carriers or both and then, if necessary, shaping the product into the desired form. When desired, the above-described formulations adapted to give sustained release of the active pharmaceutical ingredient may be employed. Sustained release formulations well known to the art include the use of liposomes, biocompatible polymers, bolus injection, or continuous infusion.

Medium-chain fatty alcohols can also be used in combination with other therapeutically active agents such as cytotoxic anticancer agents or other anticancer agents (immune modulating or regulating drugs or therapeutic vaccines or anti-angiogenesis drugs, medium-chain fatty acids or triglycerides thereof, etc.) or immune suppressive drugs (including anti-inflammatory drugs). The individual components of such combinations may be administered either sequentially or simultaneously in separate or combined pharmaceutical formulations. The combination referred to above may conveniently be presented for use in the form of a pharmaceutical formulation and thus pharmaceutical formulations comprising a combination defined above together with a pharmaceutically acceptable carrier thereof comprise a further aspect of the invention.

Alternatively, at least a pharmacologically effective amount of a human colony stimulating factor (e.g., G-CSF or GM-CSF) or a human erythropoietin may be simultaneously or separately administered with the medium-chain fatty alcohol or alkyl ester thereof. Simultaneous administration may reduce the amount of colony stimulating factor or erythropoietin needed to stimulate hematopoiesis or another affect of the colony stimulating factor or erythropoietin. Separate administration of the colony stimulating factor or erythropoietin may be before and/or after administration of the medium-chain fatty alcohol or alkyl ester thereof.

EXAMPLE

The following further illustrates the practice of this invention but is not intended to be limiting thereof.
Chemoprotection Studies: In vivo Induction of Immune Cell Proliferation or Protection By Medium-Chain Fatty Alcohol.

Female C57BL/6 mice, 6 to 8 weeks old, were immunosuppressed by treatment with 200 mg/kg of cyclophosphamide (CY) administered intravenously at day 0. To examine the immunoprotective effect of the medium-chain fatty alcohol, mice were pre-treated at day −3, −2 and −1 by oral administration of the compound. Mice were sacrificed at day +5 by cardiac puncture and cervical dislocation. After the sacrifice, tissues were crushed in PBS buffer and cells were counted on a hemacytometer.

A significant increase in bone marrow white cell count was observed with oral pre-treatment with decanol (FIG. 1). Further, some treated animals return to a "baseline level" in terms of the bone marrow white cell count as compared to non-immunosuppressed animals (control).

Figure 2:
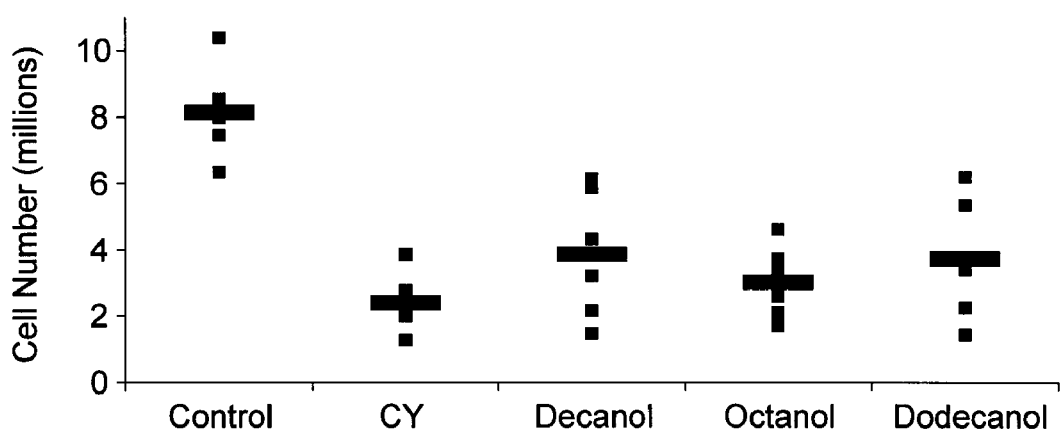
FIG. 2 shows the effect of octanol, decanol, or dodecanol on peripheral white blood cell count.

Also, a nonsignificant increase in peripheral white blood cell count was observed with octanol, decanol, or dodecanol (FIG. 2).

Figure 3A:
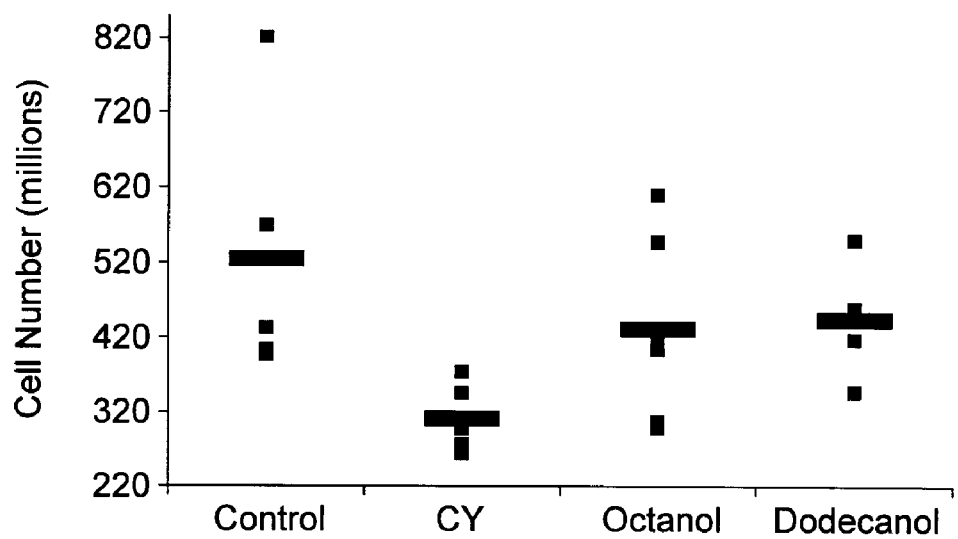
FIG. 3A shows octanol and dodecanol effects and FIG. 3B shows octanol and decanol effects.
Figure 3B:
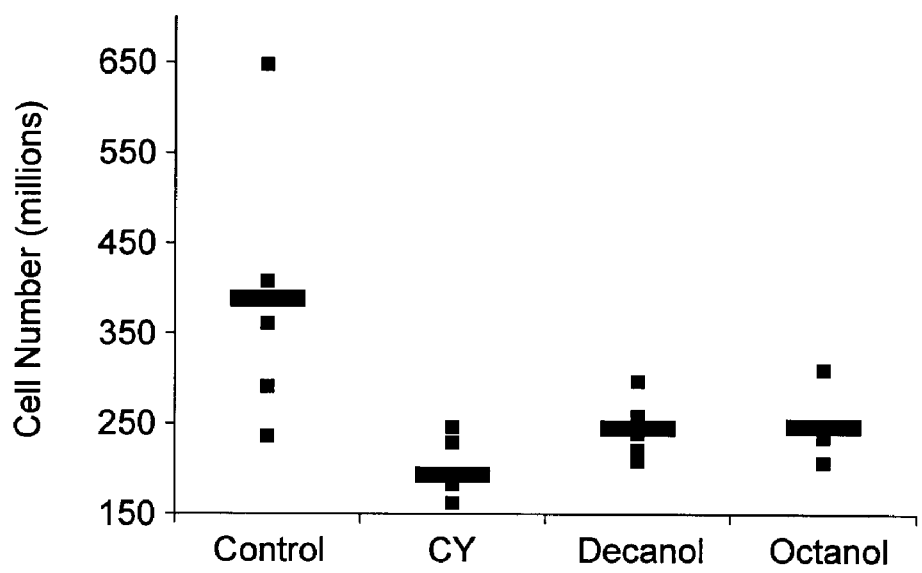

Furthermore, a significant increase in spleen red cell count was observed with oral pre-treatment with octanol, decanol, or dodecanol (FIG. 3).

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of increasing the number of red and/or white blood cells in a patient in need of treatment to increase their number of red and/or white blood cells, said method comprising oral administration to said patient of a composition consisting of a pharmacologically effective amount of one or more compounds described by formula 1:

$$H_3C(CH_2)_nOH \qquad (1)$$

wherein n=7-11 and one or more pharmaceutically acceptable carriers or excipients.

2. The method of claim 1, wherein decanol is one of said one or more compounds.

3. The method of claim 1, wherein dodecanol is one of said one or more compounds.

4. The method of claim 1, wherein at least one compound of said composition is orally administered such that the concentration is greater than 1 μM in blood.

5. The method of claim 1, wherein increasing the number of red and/or white blood cells is carried out during the course of treating myelosuppression arising from chemotherapy in said patient.

6. The method of claim 1, wherein increasing the number of red and/or white blood cells is carried out during the course of treating myelosuppression arising from radiotherapy in said patient.

7. The method of claim 1, wherein increasing the number of red and/or white blood cells is carried out during the course of treating neutropenia arising from chemotherapy in said patient.

8. The method of claim 1, wherein increasing the number of red and/or white blood cells is carried out during the course of treating neutropenia arising from radiotherapy in said patient.

9. The method of claim 1, wherein increasing the number of red and/or white blood cells is carried out during the course of treating anemia arising from chemotherapy in said patient.

10. The method of claim 1, wherein increasing the number of red and/or white blood cells is carried out during the course of treating anemia arising from radiotherapy in said patient.

11. The method of claim 1, wherein increasing the number of red and/or white blood cells is carried out during the course of treating neutropenia arising from a hematologic disease, or infection, or a nutritional deficiency, or drug-induced neutropenia in said patient.

12. The method of claim 1, wherein increasing the number of red and/or white blood cells is carried out during the course of treating anemia arising from chronic renal failure, or end-stage renal disease, or arising from a medical or surgical procedure, or drug-induced anemia in said patient.

13. The method of claim 1, further comprising administration to said patient of a second composition comprising a pharmacologically effective amount of another therapeutically active agent.

14. The method of claim 13, wherein said another therapeutically active agent is a human colony stimulating factor.

15. The method of claim 14, wherein said human colony stimulating factor is G-CSF or GM-CSF.

16. A method of increasing the number of red blood cells in a patient in need of treatment to increase their number of red blood cells, said method comprising oral administration to said patient of a composition consisting of a pharmacologically effective amount of one or more compounds described by formula 1:

$$H_3C(CH_2)_nOH \qquad (1)$$

wherein n=7-11 and one or more pharmaceutically acceptable carriers or excipients.

17. The method of claim 16, wherein decanol is one of said one or more compounds.

18. A method of increasing the number of white blood cells in a patient in need of treatment to increase the number of white blood cells, said method comprising oral administration to said patient of a composition consisting of, as an active ingredient, a pharmacologically effective amount of one or more compounds described by formula 1:

$$H_3C(CH_2)_nOH \qquad (1)$$

wherein n=7-11 and one or more pharmaceutically acceptable carriers or excipients.

19. The method of claim 18, wherein decanol is one of said one or more compounds.

20. The method of claim 13, wherein said another therapeutically active agent is human erythropoietin.

21. The method of claim 20, wherein said human erythropoietin is simultaneously administered with said one or more compounds.

22. The method of claim 20, wherein said human erythropoietin is separately administered from said one or more compounds before and/or after administration of said one or more compounds.

23. The method of claim 14, wherein said human colony stimulating factor is simultaneously administered with said one or more compounds.

24. The method of claim 14, wherein said human colony stimulating factor is separately administered from said one or more compounds before and/or after administration of said one or more compounds.

25. The method of claim 16, further comprising administration to said patient of a second composition comprising a pharmacologically effective amount of another therapeutically active agent.

26. The method of claim 25, wherein said another therapeutically active agent is human erythropoietin.

27. The method of claim 18, further comprising administration to said patient of a second composition comprising a pharmacologically effective amount of another therapeutically active agent.

28. The method of claim 27, wherein said another therapeutically active agent is a human colony stimulating factor.

29. The method of claim 28, wherein said human colony stimulating factor is G-CSF or GM-CSF.

30. The method of claim 1, wherein the patient has or is at risk of developing anemia, leukopenia, neutropenia, agranulocytosis, thrombocytopenia, myelosuppression, hematologic disease, infection, nutritional deficiency, chronic renal failure, and/or end-stage renal disease, and/or the patient is treated with a chemotherapeutic agent or radiotherapy before, during, or after said administration.

* * * * *